US006379893B1

United States Patent
Campbell et al.

(10) Patent No.: US 6,379,893 B1
(45) Date of Patent: Apr. 30, 2002

(54) EVALUATION OF ADENOCARCINOMA OF THE PROSTATE AND BREAST USING ANTI-DYSTROGLYCAN ANTIBODIES

(75) Inventors: Kevin P. Campbell, Iowa City, IA (US); Michael Henry, Maynard, MA (US); Michael B. Cohen, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/594,433

(22) Filed: Jun. 15, 2000

Related U.S. Application Data
(60) Provisional application No. 60/141,149, filed on Jun. 25, 1999.

(51) Int. Cl.$^7$ ................................................. C12O 1/68
(52) U.S. Cl. .................... 435/6; 435/240.2; 435/252.3; 435/320.1; 530/350; 536/23.5
(58) Field of Search ....................... 435/6, 240.2, 252.3, 435/320.1; 530/350; 536/23.5

(56) References Cited

U.S. PATENT DOCUMENTS

| | | | |
|---|---|---|---|
| 5,449,616 A | * 9/1995 | Campbell et al. | ........ 435/240.1 |
| 5,686,073 A | 11/1997 | Campbell et al. | |

OTHER PUBLICATIONS

Henry and Campbell, *Curr. Opin. Cell Biol.* 8: 625–631 (1996).
Durbeej et al., *J. Histochem. Cytochem.* 46: 449–457 (1998).
Ahmad and Hart, *Crit. Rev. Oncol./Hematol.* 26: 163–173 (1997).
Ali et al., *Cell* 11: 115–126 (1977).
Hayman et al., *J. Cell. Biol.* 88: 352–357 (1981).
Daly et al., *Oncogene* 8: 1721–1729 (1993).
Driouch et al., *Cancer Res.* 58: 2081–2086 (1998).
Williamson et al., *Hum. Mol. Genet.* 6: 831–841 (1997).
Henry et al., "Reduced expression of dystroglycan in prostate and breast cancer", American Journal of Human Genetics, vol. 65, Oct. 1999, p. A130 XP000974376 abstract.
Losasso et al., "Anomalous dystroglycan in carcinoma cell lines", FEBS Letters, vol. 484, Nov. 10, 2000, pp. 194–198, XP002155680 the whole document.

* cited by examiner

*Primary Examiner*—W. Gary Jones
*Assistant Examiner*—Janell E. Taylor
(74) *Attorney, Agent, or Firm*—Kevin M. Farrell

(57) ABSTRACT

Disclosed is a method for diagnosing the tumorigenic grade of a malignant tissue. The method entails determining the amount of dystroglycan protein of the malignant tissue relative to a standard. Suitable methods for determining the amount of dystroglycan protein of the tissue are provided, and include measuring the amount of mRNA transcripts which encode dystroglycan, and also performing western blot analysis or immunofluorescence analysis on the tissue components to detect α-dystroglycan or β-dystroglycan. An antibody probe which binds specifically to the C-terminus of β-dystroglycan, is provided. This method is applicable to human malignant tissue, especially adenocarcinoma, and preferably prostate or mammary adenocarcinoma. This method can also be applied to the detection of a cancerous disease state in a tissue of a patient, with a decreased level of dystroglycan protein being indicative of the presence of cancer. Also disclosed is a method for determining the prognosis of a patient afflicted with a malignancy by determining the expression level of the dystroglycan gene in a tissue sample of the malignancy, and comparing the expression level to a standard, with a decreased level of dystroglycan expression being indicative of unfavorable prognosis. A method for identifying an individual at risk for the development of cancer, or an individual at risk for the recurrence of cancer after treatment, is also disclosed. Similarly, a method for identifying individuals at risk for developing cancer by screening for mutations in the dystroglycan genes of the individual is also provided. One such mutation is the allelic loss of human chromosome 3p21.

19 Claims, No Drawings

EVALUATION OF ADENOCARCINOMA OF THE PROSTATE AND BREAST USING ANTI-DYSTROGLYCAN ANTIBODIES

This application claims benefit of Provisional Appln No. 60/141,149 Jun. 25, 1999.

BACKGROUND OF THE INVENTION

Dystroglycan is an integral membrane protein that links the cytoskeleton and extracellular matrix (*Curr. Opin. Cell Biol.* 8: 625–631 (1996)). Although first discovered in skeletal muscle as a component of the dystrophin-glycoprotein complex, it has now become clear that dystroglycan is expressed in many cell types and tissues. An underlying theme in the expression pattern of dystroglycan is that it is expressed in most cell types directly associated with basement membranes (e.g., muscle, peripheral nerve, and epithelia) (*J. Histochem. Cytochem.* 46: 449–457 (1997)). Dystroglycan null mouse embryos fail to progress beyond the early egg cylinder stage (5.5 days) and manifest structural and functional defects in Reichert's membrane, one of the first basement membranes that form in the rodent embryo (*Hum. Mol. Genet.* 6: 831–841 (1997)). Moreover, dystroglycan has recently been shown to be required for the formation of basement membranes in embryoid bodies, a system that models early embryonic development (*Cell* 95: 859–870 (1998)). Dystroglycan is also required for the organization of laminin, a key extracellular matrix ligand for dystroglycan, on cell surfaces (*Cell* 95: 859–870 (1998)). Taken together these observations suggest a model whereby dystroglycan organizes laminin, and perhaps other matrix molecules, on the cell surface in a manner that is important for the formation of basement membranes at the tissue level of organization.

Longstanding observations in the field of cancer biology indicate that transformed cells exhibit numerous aberrant interactions with the extracellular matrix in general and more specifically with basement membranes. For example, transformed cells typically exhibit a marked reduction of fibronectin (*Cell* 11: 115–126 (1978)) and laminin (*J. Cell. Biol.* 88: 352–357 (1981)) associated with their surfaces, compared to non-transformed controls. Moreover, invasive or metastatic cancers of epithelial origin often exhibit gross disruptions in the integrity of their underlying basement membranes (*Lab Invest.* 49: 140–147 (1983)). This is thought to reflect the role of basement membranes as a physical barrier between the epithelium and stroma, and the necessity that this barrier be breached in order for epithelioid cancer cells to invade the stroma as they metastasize to distant sites. On the other hand, many basement membrane proteins may also provide positive trophic support for transformed cells, and in some types of neoplastic disease, invasive lesions may retain their association with basement membrane proteins (*Lab Invest.* 49: 140–147 (1983)). These behaviors of tumor cells are quite complex and involve numerous mechanisms including secretion of matrix degrading enzymes and altered expression of matrix proteins, and their receptors, on the cell surface (*Crit. Rev. Oncol. Hematol.* 26: 163–173 (1997)). The demonstrated ability of dystroglycan to bind and organize laminin on the cell surface, and its requirement for the de novo assembly of basement membranes, suggests that dystroglycan might be involved in cancer cell invasion and metastasis. One possibility is that a reduction or ablation of dystroglycan expression in transformed cells may alter cell interactions (e.g., anchorage) with the extracellular matrix, or alter the integrity of cell basement membranes in such as way as to promote the ability to invade tissues or metastasize.

SUMMARY OF THE INVENTION

The present invention relates in one aspect, to a method for diagnosing the tumorigenic grade of a malignant tissue, the method comprising determining the amount of dystroglycan protein of the malignant tissue relative to a standard. In one embodiment, the amount of dystroglycan protein of the tissue is determined by measuring the amount of mRNA transcripts which encode dystroglycan, accomplished for example by northern blot analysis of the RNA in the tissue or polymerase chain reaction to specifically amplify dystroglycan mRNA transcripts or a segment thereof. In another embodiment, the amount of dystroglycan protein in the tissue is determined by performing western blot analysis or immunofluorescence analysis on the tissue components to detect α-dystroglycan or β-dystroglycan. An antibody probe suitable for such analyses, which binds specifically to the C-terminus of β-dystroglycan, is provided. This method is applicable to human malignant tissue, especially adenocarcinoma, and preferably prostate or mammary adenocarcinoma.

In another aspect, the present invention relates to a method for determining the prognosis of a patient afflicted with a malignancy, the method comprising determining the expression level of the dystroglycan gene in a tissue sample of the malignancy, and comparing the expression level to a standard, with a decreased level of dystroglycan expression being indicative of unfavorable prognosis. The expression level of the dystroglycan gene may be determined by determining the amount of mRNA transcripts of the gene or by determining the level of the dystroglycan protein relative to a standard amount of said transcripts or protein. This method can also be applied to detection of a cancerous disease state in a tissue of a patient, a decreased level of dystroglycan protein being indicative of the presence of cancer.

In another aspect, the present invention relates to a method for identifying an individual at risk for the development of cancer, or an individual at risk for the recurrence of cancer after treatment, the method comprising determining the level of expression of the dystroglycan gene in tissue samples from an individual, and comparing the dystroglycan expression level in the sampled tissue with a normal dystroglycan expression level, a decreased level of dystroglycan expression being indicative of high risk for development or recurrence of cancer.

In another aspect, the present invention relates to a method for identifying individuals at risk for developing cancer comprising, screening for mutations in the dystroglycan genes of the individual. One such mutation is the allelic loss of human chromosome 3p21. The mutations may be identified by amplifying coding regions of the dystroglycan gene of the individual by polymerase chain reaction, and then examining the amplified regions for mutations which affect the function of the dystroglycan protein product.

DETAILED DESCRIPTION OF THE INVENTION

The present invention stems from the finding that dystroglycan protein expression is down-regulated or undetectable in malignant cells compared to non-malignant cells of the same cell type. Studies presented in the Exemplification section below, performed on human breast adenocarcinomas and human prostate adenocarcinomas indicate a significant reduction in dystroglycan protein expression compared to normal epithelial structures. The observed trend in these studies is that dystroglycan expression is reduced more extensively in high grade, invasive lesions.

Tumor cells arise in a patient due to a loss of the natural growth control inherent in every cell. This loss is a multistep process of events which often progresses in a predictable order. Applicants propose that the observed correlation of reduction of dystroglycan expression with the advancement of tumorigenesis be exploited in the diagnosis of human neoplasia, using the presence or absence of dystroglycan protein as a molecular marker for the more advanced stages of tumorigenesis of neoplastic cells.

One aspect of the present invention is a method for diagnosing the tumorigenic grade of a malignant tissue by determining the amount of dystroglycan protein of the malignant tissue relative to a standard. The term "tumorigenic grade" is used herein to describe how far the process of growth control loss has progressed at the time of tumor diagnosis. Experiments detailed in the Exemplification section which follows examined prostate and mammary tumors of high grade (e.g., higher than grade 3 of the Gleason grade for prostate tumorigenesis) for dystroglycan expression. The tumors examined had progressed into or past the stage of tumorigenesis where metastatic invasion of the tumor into other tissues of the body occurs. An observed reduction or loss of dystroglycan expression in 100% of the high grade tumors examined indicates that the dystroglycan molecule can serve as a molecular marker for tumorigenesis progression into a metastatic stage of disease.

The amount of dystroglycan protein present in a malignant tissue relative to a standard can be determined by several methods of analysis. In all methods of analysis, the standard should be determined by performing the same method of analysis on a healthy, non-tumorigenic tissue which resembles as closely as possible the tissue type from which the tumor originally arose. Often, this will be healthy tissue which surrounds the tumor. Experiments in the Exemplification section below determined the amount of dystroglycan in a malignant tissue by specifically detecting β-dystroglycan. However, detection of levels of α-dystroglycan is also indicative of the total dystroglycan present.

One form of analysis for determining the amount of dystroglycan protein present in a malignant tissue is measuring the amount of mRNA transcripts which encode the dystroglycan protein, present in the cells of the malignant tissue. Detection of a significantly reduced amount of dystroglycan mRNA is indicative of reduced dystroglycan protein product. One of skill in the art will recognize however, that an indication of standard levels of dystroglycan mRNA may not necessarily be reflected by standard levels of the dystroglycan protein. Such a negative result could be followed up with a direct measurement of the dystroglycan protein present in the malignant tissue, described below, to rule out the possibility of mutations in translation or processing of the dystroglycan protein which cause a reduction in functional dystroglycan protein in the tissue.

Dystroglycan mRNA can be measured by a variety of methods. These methods include, without limitations, Northern blot analysis (also known as RNA blot analysis) of the tissue RNA transcripts. This can be performed on total RNA or any fractionation of total RNA (e.g., mRNA or polyA mRNA). In addition, in situ hybridization can be performed to detect the dystroglycan transcripts within the cells of the tissue.

Another method for quantitating dystroglycan mRNA is by polymerase chain analysis (PCR) or by reverse PCR. The appropriate primers are used to specifically amplify dystroglycan message, either the complete message, or one or more segments thereof, quantitatively from both the malignant tissue. In addition, the analogous message is amplified from the standard tissue as a control, and the two relative amounts of message are compared to determine if the malignant tissue has reduced dystroglycan expression.

The coding sequence of dystroglycan is known in the art. Identification and quantitation of dystroglycan mRNA transcripts of a tissue or cells of a tissue by the methods described above is within the ability of one of average skill in the art through no more than routine experimentation. In addition, the above described methods of northern blot analysis and PCR can also be used to identify mutations in the dystroglycan message which lead to reduced dystroglycan protein function (e.g., truncations, amino acid substitutions, reduced translation).

As mentioned above, the amount of dystroglycan protein of a malignant tissue can also be determined directly by methods which identify the dystroglycan protein. The translation product of the single dystroglycan gene is processed into two polypeptides, α-dystroglycan and β-dystroglycan. Detection of either α-dystroglycan, β-dystroglycan, or both polypeptides, can be used to determine the amount of dystroglycan protein in a cell or tissue. This is generally performed by use of an affinity reagent which specifically binds to dystroglycan, or a uniquely identifying component thereof. The most commonly used affinity reagent is an antibody (either polyclonal or monoclonal). Several antibodies are currently known in the art which specifically bind dystroglycan.

In one embodiment of the present invention, a combination of antibodies, or other affinity reagents, which recognize and bind different regions of the dystroglycan molecule, are used in the methods describe below to identify aberrant dystroglycan molecules which are expressed, but which have impaired function. Usually, an affinity reagent such as an antibody, specifically binds a distinct portion of the molecule. Molecules which lack the distinct portion to which the antibody binds, will not be identified. One such antibody is AP83, described in the Exemplification below, which binds the C-terminus of β-dystroglycan.

Affinity reagents which specifically bind dystroglycan can be used in a variety of assays known in the art to quantitatively or semi-quantitatively detect the presence of dystroglycan on a tissue. One such assay is western blot analysis, wherein an antibody probe is used to identify the specific protein of interest, or a uniquely identifying component thereof, from the tissue components. Another such assay is immunofluorescence analysis, which has the advantage of identifying the specific location and distribution of one or more protein(s) of interest, or a uniquely identifying component thereof, in the intact cells of the tissue.

The methods described herein are applicable to mammalian systems and tumors in general, and are preferably to be applied to human systems and tumor tissues. In one embodiment, the malignant tissue is a carcinoma, preferably an adenocarcinoma (e.g., prostate adenocarcinoma or mammary adenocarcinoma). The methods of the present invention described herein are expected to have particular use when diagnosing tumors which exhibit a high frequency of allelic loss of the chromosomal region where the dystroglycan gene resides, 3p21 (e.g., mammary carcinoma, small cell and non-small cell lung carcinoma, squamous cell carcinoma of the head and neck, cervical carcinoma).

Another aspect of the present invention relates to a method for determining the prognosis of a patient afflicted with a malignancy. Because the grade of tumorigenesis is a direct indicator of the aggressiveness of the malignancy, information regarding the grade of the tumor is useful for determining the prognosis of the afflicted patient. The method involves determining the expression level of the dystroglycan gene in a tissue sample of the malignancy of the patient, and comparing the levels to a standard. A decreased level of dystroglycan expression when compared to the standard is indicative of a more advanced grade of tumor, and an unfavorable prognosis. The standard level is determined by analysis of a healthy, non-tumorigenic tissue obtained from the patient, which resembles as closely as possible the tissue type from which the tumor originally arose. The expression level of the dystroglycan gene in a tissue sample of the malignancy or in a control tissue, can be accomplished by quantitation of the dystroglycan mRNA or the dystroglycan protein within the tissue sample, as described above. Alternatively, the tissue of the malignancy can be examined for chromosomal abnormalities which indicate disruption or loss of either of the dystroglycan gene. Methods for this type of examination are discussed below.

Another aspect of the present invention relates to a method for identifying individuals at risk for the development of cancer, or individuals at risk for the recurrence of cancer after treatment. Implication of the contribution of reduced dystroglycan expression in malignant tumor progression indicates that individuals which are homozygous for a non-functional or reduced functional dystroglycan gene have a genetic predisposition for the development of malignant tumors in which loss of dystroglycan function plays a role. Such an individual can be identified by determining the level of expression of the dystroglycan gene in tissue samples from the individual, and comparing the level of expression to a normal standard expression level. A decreased level of dystroglycan expression is indicative of an individual who is at high risk for development or recurrence of cancer. Such an individual is especially at risk for the development of cancers resulting from tumors which exhibit a high frequency of allelic loss of the chromosomal region where the dystroglycan gene resides, 3p21 (e.g., mammary carcinoma, small cell and non-small cell lung carcinoma, squamous cell carcinoma of the head and neck, cervical carcinoma). The tissue from which the sample is derived may be any tissue, somatic or germ line. In one embodiment, the sample is taken from a tissue which is implicated as having a higher probability for tumor development (e.g., mammary epithelium, or prostate epithelium). Such a high probability may be identified by a family history, environmental influences known to induce specific types of tumors, or alternatively by previous tumor diagnosis and treatment. A normal, standard expression level is determined for the particular tissue which is examined, by examination of like tissues from a statistically relevant number of healthy individuals.

An alternative method of identifying individuals at risk for developing cancer is screening individuals for mutations in their dystroglycan gene. Such mutations include gross chromosomal rearrangements (e.g., allelic loss of human chromosome 3p21) and also mutations in gene sequence which affect expression of a functional dystroglycan protein. Mutations in gene sequence can be identified by amplifying coding regions of the dystroglycan genes of an individual by PCR, and examining the amplified nucleic acids (e.g., by sequencing or size determination) for mutations which affect the function of the dystroglycan protein product. Coding regions can be amplified from genomic DNA, or alternatively, from mRNA. In addition, examination of non-coding region may also indicate a mutation which reduces the level of dystroglycan expression of the individual (e.g., a mutation in the regulatory sequences of a gene). One of skill in the art will recognize that additional methods exist for the identification of gene abnormalities in an individual. It is important to note that reduced expression of the dystroglycan gene may be caused by outside influences, rather than mutations within the actual dystroglycan gene. Such outside influences include, without limitation, aberrant activity of one or more regulators of the dystroglycan gene.

The present invention also relates to a method for detection of a cancerous disease state in a tissue of a patient by determining the level of the dystroglycan protein in a sample of the tissue relative to a standard level of dystroglycan protein. A decreased level of dystroglycan protein would indicate the presence, or likelihood of the development, of cancer from that tissue. As discussed above, the standard level of dystroglycan protein may be determined by examination of healthy tissue of the patient or alternatively, by examination of the same type tissue in other healthy individuals.

Another aspect of the present invention relates to treatment of a tumor which has reduced or undetectable dystroglycan expression. The observation that the dystroglycan protein level is reduced more extensively in high grade, invasive lesions, coupled with current knowledge regarding the function of dystroglycan in a cell and the current understanding regarding metastasis of tumors, strongly suggests that a loss of dystroglycan expression facilitates metastasis of tumor cells. Reintroduction of a functional dystroglycan gene is expected to inhibit the ability of the tumor cells to metastasize. Introduction of a functional dystroglycan gene into cells can be accomplished by several methods known in the art. Preferably such gene therapy is accomplished using one of several adenovirus vectors known in the art. Such vectors are useful for both blanket delivery of a gene to cells within a given physical area, and also for cell type specific delivery throughout the entire body (e.g., targeting a tumor specific antigen or marker). As an alternative to cell type specific delivery, the delivered dystroglycan gene could be under the control of a cell type specific regulatory region (e.g., a promoter which is active in tumor cells).

EXEMPLIFICATION

Clinical tissue samples were obtained from 18 human prostate malignancies, and 9 human breast malignancies. These malignancies were all of Gleason grade 3 or higher. Each tissue sample was examined for dystroglycan expression by immunofluorescence analysis, using an antibody which specifically binds C-terminal β-dystroglycan. The level of dystroglycan expression of the malignant tissues was compared to the level of dystroglycan expression of benign prostate epithelium and benign breast epithelium, obtained from normal tissue surrounding each of the malignancies. Although dystroglycan was expressed in benign prostatic and mammary epithelia, all of the malignancies examined showed significantly reduced or undetectable dystroglycan expression compared to that of the benign tissue. Immunofluorescence analysis of dystroglycan expression in the human prostate and breast tissues indicated significantly reduced expression in malignant prostatic glandular elements and in infiltrating ductal adenocarcinoma of the breast tissue. These preliminary findings strongly indicate that the degree or extent of reduction in dystroglycan expression correlates with the histological grade of the tumor.

The dystroglycan gene is localized to human chromosome 3p21. This locus has been implicated by a variety of experiments to contain one or more tumor suppressor gene (s) in breast as well as many other types of cancer (*Oncogene* 8: 1721–1729 (1993)). Moreover, recent studies have implicated this locus as demonstrating enhanced allelic loss in breast cancer metastases as compared to their primary tumor counterparts, suggesting a role for this locus in breast cancer metastasis (*Cancer Res.* 58: 2081–2086 (1998)). This suggests a genetic basis for the observed reduction or ablation of dystroglycan expression in breast cancer. However, other additional mechanisms may also influence the expression of dystroglycan in tumors.

Methods of the Invention

Antibodies. The polyclonal antibody AP83 (*Hum. Mol. Genet.* 6: 831–841 (1997)) was used in the immunofluorescence. This antibody was prepared by immunizing with an antigen containing the carboxy-terminal 15 amino acids of rabbit β-dystroglycan. Preparation of the antigen and immunization of the rabbit was by standard methods. Whole serum obtained from the immunized rabbit was then affinity purified against the immunizing peptide coupled to BSA, by standard methods.

Immunofluorescence. Frozen breast and prostate tissue was cut into 7 micron sections and applied to glass slides. Sections were blocked for 1 hr in PBS + 1% BSA. The in polyconal antibody AP83 was diluted 1:100 in PBS+1% BSA. Sections were incubated overnight in 0.3 ml of the dilated antibody solution. Sections were then washed three times in three minute intervals with 0.5 ml PBS. Fluorescent secondary antibodies were diluted to the appropriate concentration in PBS+1% BSA. Sections were incubated in 0.3 ml diluted secondary antibody for 1 hr. Sections were then washed three times in three minute intervals with 0.5 ml PBS. Coverslips were mounted on the slides and then the sections were viewed using epifluorescence microscopy.

What is claimed is:

1. A method for diagnosing the tumorigenic grade of a malignant tissue, comprising:
   a) determining the amount of dystroglycan protein of the malignant tissue relative to a standard; and
   b) comparing the amount of dystroglycan protein to said standard, wherein a decreased level of dystroglycan protein is indicative of the tumorigenic grade of the malignant tissue.

2. The method of claim 1 wherein the amount of dystroglycan protein of the tissue is determined by measuring the amount of mRNA transcripts which encode dystroglycan.

3. The method of claim 2 wherein the amount of mRNA transcripts which encode dystroglycan are measured by northern blot analysis of the RNA in the tissue.

4. The method of claim 2 wherein the amount of mRNA transcripts which encode dystroglycan are measured by subjecting mRNA isolated from the tissue cells to polymerase chain reaction to specifically amplify dystroglycan mRNA transcripts or a segment thereof.

5. The method of claim 1 wherein the amount of dystroglycan protein in the tissue is determined by performing western blot analysis on the tissue components to detect α-dystroglycan or β-dystroglycan.

6. The method of claim 5 wherein the western blot analysis is performed using an antibody probe which binds specifically to β-dystroglycan.

7. The method of claim 6 wherein the antibody probe binds specifically to the C-terminus of β-dystroglycan.

8. The method of claim 7 wherein the antibody probe is generated to the C-terminal 15 amino acids of β-dystroglycan.

9. The method of claim 8 wherein the antibody is AP83.

10. The method of claim 1 wherein the amount of dystroglycan protein of the tissue is measured by performing immunofluorescence analysis on cells of the tissue to detect α-dystroglycan or β-dystroglycan.

11. The method of claim 10 wherein the immunofluorescence analysis is performed using an antibody probe which binds specifically to β-dystroglycan.

12. The method of claim 11 wherein the antibody probe binds specifically to the C-terminus of β-dystroglycan.

13. The method of claim 12 wherein the antibody probe is generated to the C-terminal 15 amino acids of β-dystroglycan.

14. The method of claim 13 wherein the antibody probe is comprised of AP83.

15. The method of claim 1 wherein the malignant tissue is human.

16. The method of claim 15 wherein the tissue is an adenocarcinoma.

17. The method of claim 16 wherein the adenocarcinoma is a prostate adenocarcinoma.

18. The method of claim 16 wherein the adenocarcinoma is a mammary adenocarcinoma.

19. A method for detection of a cancerous disease state in a tissue of a patient comprising determining the level of dystroglycan protein in a sample of the tissue relative to a standard level of said protein, a decreased level of dystroglycan protein being indicative of the presence of cancer.

* * * * *